(12) United States Patent
Lewis, Jr. et al.

(10) Patent No.: US 11,389,832 B2
(45) Date of Patent: Jul. 19, 2022

(54) LOW-PROFILE, LOW-FREQUENCY, AND LOW-IMPEDANCE BROAD-BAND ULTRASOUND TRANSDUCER AND METHODS THEREOF

(71) Applicant: ZetrOZ Systems llc, Trumbull, CT (US)

(72) Inventors: George K. Lewis, Jr., Trumbull, CT (US); George K. Lewis, Sr., Trumbull, CT (US)

(73) Assignee: ZetrOZ Systems, LLC, Trumbull, CT (US)

( * ) Notice: Subject to any disclaimer, the term of this patent is extended or adjusted under 35 U.S.C. 154(b) by 361 days.

(21) Appl. No.: 14/899,984

(22) PCT Filed: Jun. 24, 2014

(86) PCT No.: PCT/US2014/043951
§ 371 (c)(1),
(2) Date: Dec. 18, 2015

(87) PCT Pub. No.: WO2014/210063
PCT Pub. Date: Dec. 31, 2014

(65) Prior Publication Data
US 2016/0136687 A1 May 19, 2016

Related U.S. Application Data

(60) Provisional application No. 61/838,768, filed on Jun. 24, 2013.

(51) Int. Cl.
*B06B 1/06* (2006.01)
*H01L 41/18* (2006.01)
(Continued)

(52) U.S. Cl.
CPC .......... *B06B 1/0618* (2013.01); *A61B 8/4483* (2013.01); *A61B 8/4494* (2013.01);
(Continued)

(58) Field of Classification Search
CPC ..... B06B 1/0618; B06B 1/0622; B06B 1/064; B08B 7/026; H01L 41/277; A61B 8/4483
(Continued)

(56) References Cited

U.S. PATENT DOCUMENTS

| 5,438,554 A | 8/1995 | Seyed-Bolorforosh et al. |
| 2005/0261590 A1* | 11/2005 | Ogawa .................. B06B 1/0629 600/459 |

(Continued)

FOREIGN PATENT DOCUMENTS

| EP | 0 697 257 A2 | 2/1996 |
| JP | 2005-286444 A | 10/2005 |

OTHER PUBLICATIONS

International Searching Authority, International Search Report and Written Opinion issued in counterpart International Application No. PCT/US2014/043951, dated Oct. 7, 2014.
(Continued)

*Primary Examiner* — Bryan P Gordon
(74) *Attorney, Agent, or Firm* — FisherBroyles, LLP; Andrew K. Gonsalves, Esq.

(57) ABSTRACT

An ultrasound transducer and a method of making this transducer, where the transducer includes at least two piezoelectric elements, oriented adjacent to each other in a stack. Each piezoelectric element includes a first surface which includes an electrode of a first polarity, a second surface which includes an electrode of a second polarity, a thickness between the first surface and the second surface, and an ultrasound transmitting surface. This surface does not include an electrode. The transducer also includes a first
(Continued)

electrical connection between a surface of a first of the at least two piezoelectric elements of the first polarity and a surface of a second of the at least two piezoelectric elements of the first polarity and a second electrical connection between a surface of a first of the at least two piezoelectric elements of the second polarity and a surface of a second of the at least two piezoelectric elements of the second polarity.

12 Claims, 16 Drawing Sheets

(51) Int. Cl.
*A61B 8/00* (2006.01)
*H01L 41/37* (2013.01)
*H01L 41/277* (2013.01)

(52) U.S. Cl.
CPC ............ *B06B 1/064* (2013.01); *B06B 1/0611* (2013.01); *H01L 41/183* (2013.01); *H01L 41/277* (2013.01); *H01L 41/37* (2013.01)

(58) Field of Classification Search
USPC .................................................. 310/322, 334
See application file for complete search history.

(56) References Cited

U.S. PATENT DOCUMENTS

| | | |
|---|---|---|
| 2007/0205697 A1 | 9/2007 | Chaggares et al. |
| 2008/0169728 A1* | 7/2008 | Asai ........................ H03H 3/04 |
| | | 310/334 |
| 2011/0121687 A1* | 5/2011 | Aoki ..................... B06B 1/0677 |
| | | 310/334 |
| 2012/0047717 A1 | 3/2012 | Spigelmyer et al. |
| 2013/0069484 A1 | 3/2013 | Kullervo et al. |
| 2013/0085390 A1 | 4/2013 | Nishikubo |
| 2016/0005951 A1* | 1/2016 | Yoshida ................ H01L 41/083 |
| | | 310/354 |

OTHER PUBLICATIONS

European Patent Office, European Search Report issued in counterpart European Patent Application No. EP 14818724, dated Jan. 16, 2017.

* cited by examiner

710a - 710l

775

WIRES TO
INDIVIDUAL
ELEMENTS $$\frac{\Delta l}{L} = d_{31} \cdot \frac{V}{t}$$

$$\Delta l = d_{31} \cdot \frac{L}{t} \cdot V$$

LOW-PROFILE, LOW-FREQUENCY, AND LOW-IMPEDANCE BROAD-BAND ULTRASOUND TRANSDUCER AND METHODS THEREOF

CROSS REFERENCE TO RELATED APPLICATION

The present invention is a U.S. National Phase filing under 35 U.S.C. § 371 of International Application No. PCT/US2014/043951, filed Jun. 24, 2014, and published as WO 2014/210063-A1 on Dec. 31, 2014, which claims benefit of priority from U.S. Provisional Patent Application No. 61/838,768, filed Jun. 24, 2013. The entire contents of each of the prior applications are incorporated herein by reference in their entirety.

FIELD OF THE INVENTION

This invention relates to devices and fabrication techniques that are used in low-frequency ultrasonic transducer applications such as in imaging, sonar and air ranging applications, scientific instruments such as ultrasonic anemometers, collision avoidance devices as well as for therapeutic and acoustic radiation applications.

BACKGROUND OF THE INVENTION

In generating low-frequency ultrasound, piezoelectric ceramics are excited in the thickness and length modes of vibration by electronic drivers which apply high voltages to electrodes placed on opposing surfaces of the ceramic. To give the ceramic its piezoelectric properties it is pre-poled beforehand. The location of the drive electrodes with respect to the direction of poling determines the coupling coefficient that relates the applied voltage to the mechanical strain developed in the ceramic.

Composite piezoelectric material is made by imbedding a plurality of piezoelectric ceramic elements in a matrix of polymer. A review of the prior art techniques can be found in an article by Wallace Smith; "Materials for Medical Ultrasound Imaging Transducers—A Review," IEEE, 1996 pp249-256 and in the patents cited. The classification of the composite is determined by the connectivity of the material used in its construction to the outside world. As an example: a piezoelectric ceramic imbedded in the center of an epoxy ball would be a 0-3 composite. The ceramic in this case has no connectivity to the outside world and the epoxy is connected in all three directions. If the ceramic is a rod that extends through the epoxy ball then it would form a 1-3 composite. If the ceramic was a plate that bisected the ball in half then it would be a 2-2 composite; the ceramic having connectivity to two directions and the epoxy now blocked in connectivity in the direction normal to the ceramic plate. The transducer of this invention may be of the 1-3 connectivity type, consisting of a plurality of piezoelectric elements imbedded in a polymer matrix, a matrix filled with air gaps, a matrix filled with vacuum gaps, a matrix filled with micro bubble/epoxy gaps and the alike.

The principle benefit of making transducers from composite material is threefold: there is an increase in sensitivity, a decrease in extraneous modes of vibration and an ease of acoustic matching the composite to its surrounding media. By fabricating transducers from a plurality of tall piezoelectric elements rather than a solid one the piezoelectric coupling coefficients which relate conversion of electrical to mechanical properties and vice-versa are increased.

Also, solid ceramics have many modes of vibration. If a ceramic is excited with a pulse of electrical energy all of these modes will get excited. These can include radial modes, shear modes, lateral modes, circumferential modes as well as the thickness mode. By interspersing tall piezoelectric elements with polymer the principle mode of vibration is relegated to the length of the element. All the other extraneous vibrations are quickly damped out by the polymer matrix.

Furthermore, by selecting the ratio of ceramic material to polymer the acoustic properties of the composite can be adjusted to more closely match the material in which it will operate. The ratio is called the volume fraction and for many composites this is in the vicinity of 50%.

In regards to therapeutic ultrasound applications the matrix and or material between stacks of piezoelectric components may be used to remove thermal heat away from the transducer, support the transducer stacks for durability and use to increase energy delivery in the preferred direction.

SUMMARY OF THE INVENTION

Shortcomings of the prior art are overcome and additional advantages are provided through a ultrasound transducer that includes: at least two piezoelectric elements, oriented adjacent to each other in a stack, wherein each of the at least two piezoelectric elements comprises: a first surface comprising an electrode of a first polarity; a second surface comprising an electrode of a second polarity; a thickness between the first surface and the second surface; and an ultrasound transmitting surface, not comprising an electrode; a first electrical connection between a surface of a first of the at least two piezoelectric elements of the first polarity and a surface of a second of the at least two piezoelectric elements of the first polarity; and a second electrical connection between a surface of a first of the at least two piezoelectric elements of the second polarity and a surface of a second of the at least two piezoelectric elements of the second polarity.

Shortcomings of the prior art are also overcome and additional advantages are provided through a method of making an ultrasound transducer that includes: obtaining at least two piezoelectric elements, each of the at least two piezoelectric elements comprising: a first surface comprising an electrode of a first polarity; a second surface comprising an electrode of a second polarity; a thickness between the first surface and the second surface; and an ultrasound transmitting surface, not comprising an electrode; orienting the at least two piezoelectric elements in the stack to enable the transducer to transmit ultrasound from the ultrasound transmitting surfaces of the at least two piezoelectric elements; and electrically coupling the at least two piezoelectric elements together in parallel in a stack, the electronically coupling comprising: electrically coupling a surface of a first of the at least two piezoelectric elements of the first polarity to a surface of a second of the at least two piezoelectric elements of the first polarity; and electrically coupling a surface of a first of the at least two piezoelectric elements of the second polarity to a surface of a second of the at least two piezoelectric elements of the second polarity.

Shortcomings of the prior art are also overcome and additional advantages are provided through an ultrasound transducer that includes: at least two piezoelectric elements, oriented adjacent and positioned parallel to each other in a stack, wherein each of the at least two piezoelectric elements comprises: a first surface comprising an electrode of a first polarity; a second surface comprising an electrode of a second polarity, wherein the first surface and the second surface define a height of the piezoelectric element; a thickness between the first surface and the second surface, wherein the height is at least three times greater than the thickness; and an ultrasound transmitting surface, not comprising an electrode; a first electrical connection between a surface of a first of the at least two piezoelectric elements of the first polarity and a surface of a second of the at least two piezoelectric elements of the first polarity; and a second electrical connection between a surface of a first of the at least two piezoelectric elements of the second polarity and a surface of a second of the at least two piezoelectric elements of the second polarity.

Other embodiments and aspects of the invention are described in detail herein and are considered a part of the claimed invention. Other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

DETAILED DESCRIPTION OF THE INVENTION

Embodiments of the present invention include a transverse mode low-profile, low-frequency and low-impedance ultrasonic transducer from a parallel stack of piezoelectric materials, including but not limited to, ceramics, composites, and/or polyvinylidene fluoride, and, optionally, interleaved materials, and construction thereof. Embodiments of the present invention include transducers and methods of making transducers with high transmit sensitivity and aspect ratios. Embodiments of the present invention can also be fabricated with electronic lateral focusing capabilities. In addition to transmitting ultrasound, embodiments of the present invention can also receive ultrasound.

Figure 1:
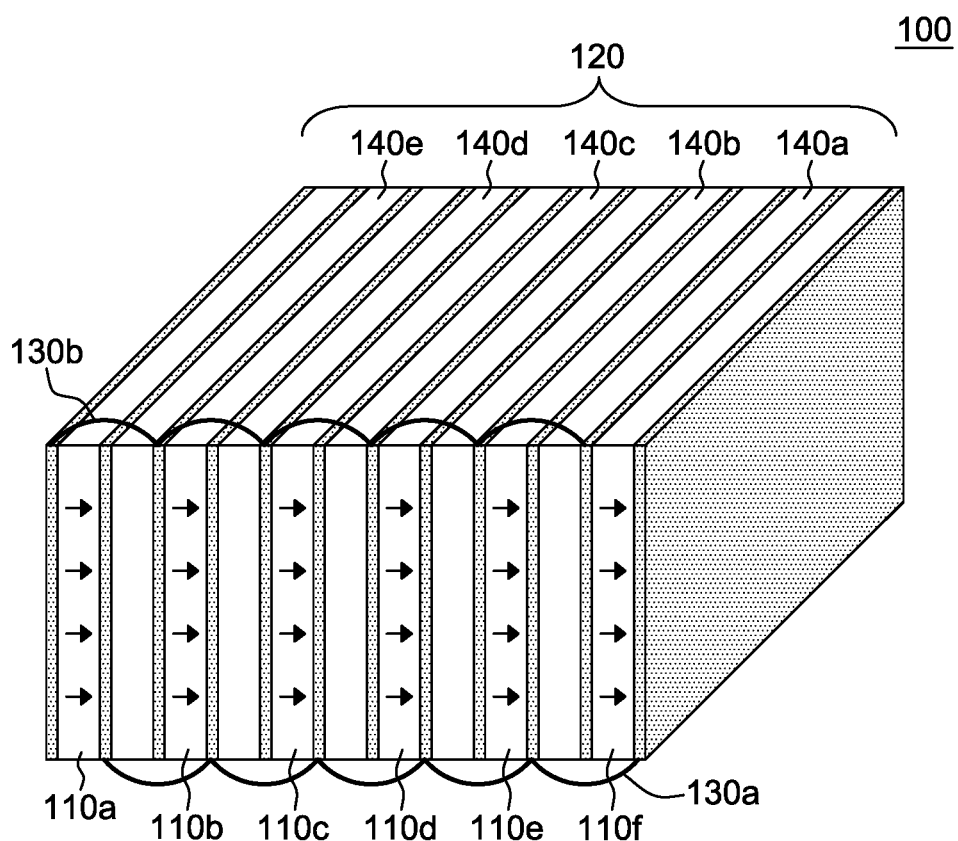
FIG. 1 depicts aspects of an embodiment of the present invention.

FIG. 1 is an embodiment of an ultrasound transducer 100 of the present invention. In this embodiment, the ultrasound transducer includes piezoelectric elements 110a-110f oriented in a stack 120. Although there are six piezoelectric elements pictured in FIG. 1, this is just an example of a possible embodiment. Embodiments of the present invention may include two or more piezoelectric elements, and both the number of elements and the number of stacks can vary across embodiments of the present invention. For example, the number of piezoelectric elements 110-110f and stacks 120 in a given transducer 100 can vary based on the desired impedance. Specifically, the electrical impedance of the transducer can be tuned by adding more elements. For example, a 1×1×1 cm volume could have 10 piezoelectric stacks, or 10000 piezoelectric stacks. The latter configuration would result in a transducer with a lower impedance, however both these configurations would both have the same surface area. Therefore, the latter configuration would produce more energy at the same voltage level input. On the other hand, with sufficient voltage the higher-impedance transducer would be able to produce an equivalent power.

The transducers of the present invention maintain a lower electrical impendence than traditional transducers of the same thickness. For example, a stack of piezoelectric elements created in accordance with the methods described herein is of a given thickness. When the impedance of this transducer, which like the transducer of FIG. 1, is fabricated from a stack of piezoelectric elements, is compared to the impendence of a transducer of the same thickness that has one piezoelectric element that is the same thickness as the stack of the transducer of the present invention, the electrical impedance of the transducer of the present invention is less than an electrical impendence of the single element transducer. Despite the difference in impedance, the frequency of the two transducers may be equivalent.

Figure 2:
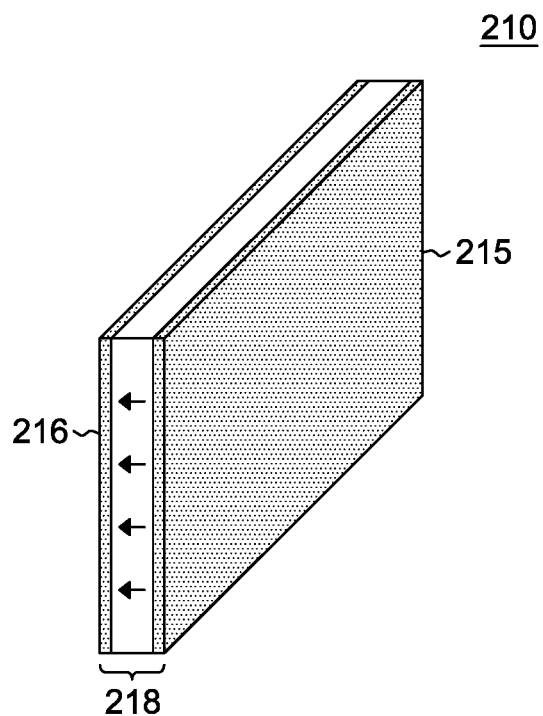
FIG. 2 depicts aspects of a piezoelectric elements utilized in embodiments of the present invention.

The piezoelectric elements 110a-110f are pictured as rectangular plates, an example of which is seen in FIG. 2. FIG. 2 illustrates a plate of piezoelectric material that is pre-poled across its thickness.

Figure 3:
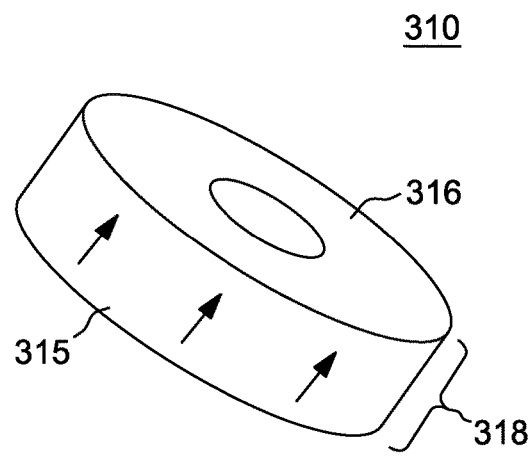
FIG. 3 depicts aspects of a piezoelectric elements utilized in embodiments of the present invention.

However, in further embodiments of the invention, elements of different shapes (as well as varying sizes) may be utilized, including circular disks, such as the piezoelectric element of FIG. 3. FIG. 3 illustrates a ring piezoelectric element poled across its thickness with a radial resonance that may be used for stacking the piezoelectric elements.

Utilizing circular disks, like the one in FIG. 3, may increase the radial resonance of the resultant transducer. Both FIG. 2 and FIG. 3 offer a more detailed view of a piezoelectric element utilized in embodiments of the present invention.

By varying the shapes of the piezoelectric elements 110a-110f, embodiments of the present invention include low-profile and low-impedance transverse or radial mode piezoelectric composite and stack transducers, having large element aspect ratios, which are fabricated from laminates of poled piezoelectric material. The fabrication and the use of laminates is discussed in greater detail later.

Referring first to FIG. 2, the piezoelectric element, a plate 210 includes a first surface 215 that includes an electrode of a first polarity, in this non-limiting embodiment, a ground electrode and a second surface 216 that includes an electrode of a second polarity, in this non-limiting embodiment, a power electrode. In the pictured embodiment, the ground electrode is the entire first surface 215 and the power electrode is the entire second surface 216. This quality may vary in further embodiments. As seen in FIG. 1, the transducer in this invention has electrodes on non-transmission faces of each piezoelectric that makes up the entire transducer to maintain the electric field within each individual piezoelectric element. Because of the use of more than one piezoelectric element, in embodiments of the transducer of the present invention, the transducer has multiple individual signal and ground electrodes. In embodiments of the present invention, the ultrasound transmitting surfaces of the piezoelectric elements are not the surfaces that have electrodes.

In FIG. 2, the portion of each piezoelectric element between the first surface 215 and the second surface 216 is a thickness 218, across which the plate 210 is pre-poled.

Referring to FIG. 3, the piezoelectric element, a disk 310 includes a first surface 315 that includes an electrode of a first polarity, in this example, a ground electrode and a second surface 316 that includes an electrode of a second polarity, in this example, a power electrode. Power and ground electrodes are given as examples of electrode types, but embodiments of the invention are not limited to these electrode types. In the pictured embodiment, the ground electrode is the entire first surface 315 and the power electrode is the entire second surface 316. Like with FIG. 2, this quality may vary in further embodiments. In FIG. 3, in-between the first surface 315 and the second surface 316 is a thickness 318, across which the plate 310 is pre-poled.

Returning to FIG. 1, the piezoelectric elements 110a-110f are electrically coupled with at least two wires 130a-130b. The number of wires 130a-130b can vary, but the elements may be wired together such that like poles of the piezoelectric elements are connected together across the piezoelectric elements 110a-110f. Thus, the elements 110a-110f are wired in the stack in parallel Although FIG. 1, as well as some additional figures, show the use of at least two wires 130a-130b to form electrical connections, any type of electrical connection, including placing the electrodes in direct contact with each other, is utilized across embodiments of the present invention. If an embodiment utilizes wires, they may be flexible to accommodate the movement of the transducer while in operation.

In the embodiment of FIG. 1, the piezoelectric elements 110a-110f are oriented in a stack such that there is space 140a-140e between each two piezoelectric elements 110a-110f. In embodiments where the transducer includes more than one space 140a-140e, the spaces are equivalent in length. The space 140a-140e (also referred to as a distance) prevents the transfer of ultrasound from one of the piezoelectric elements 110a-110f to an adjacent piezoelectric elements 110a-110f, and reduces the acoustic impendence of the transducer.

Some embodiments of the present invention do not include any spacing between piezoelectric elements 110a-110f. Additionally, in embodiments of the present invention, adjacent piezoelectric elements may be spaced in a stack, while others are stacked next to each other with no space in-between the elements.

The spacing of the piezoelectric elements 110a-110f is not determinative of the impedance aspect of the invention. In fact, in various embodiments of the present invention, these elements are spaced at different distances, or not spaced at all, and still have the same "electrical input" impedance. Acoustically however, the spacing of the piezoelectric elements 110a-110f generates a unified wave-front, which emanates directionally from the transducer.

In an embodiment of the present invention, in order to obtain a desired acoustic property, the spacing of the piezoelectric elements 110a-110f is adjusted at less than a wavelength apart, so when the mechanical pressure wave leaves the transducer actuating surface the pressure wave looks "uniform" across the front of the various piezoelectric elements 110a-110f, also referred to as actuating plates.

When the present method is used to construct a transducer with the piezoelectric elements 110a-110f spread further apart, the individual piezoelectric elements 110a-110f will start acting as individual transducers (if the wavelength is small compared to the thickness of the plate) or as an acoustic point source (if the wavelength is large compared to the thickness of the plate). Thus, there is an acoustical phenomena based on spacing of the plates, thickness of the plates, and frequency of operation of the plates.

In an embodiment of the present invention, the piezoelectric elements 110a-110f may be ceramic. In the transducer of FIG. 1, the space 140a-140e between each two of the piezoelectric elements 110a-110f is filled with a filler material. Thus, the present technique includes a fabrication method for making thick (low frequency) 1-3 composite transducer material with an arbitrary fill factor. Regarding the filler material, embodiments of the technique include utilizing a fabrication method where the extent of the composite in the invention can be expanded by the lamination of larger piezoelectric elements, including but not limited to, larger plates of piezoelectric material.

In further embodiments, of the present invention, which are discussed later, the space 140a-140e between each two of the piezoelectric elements 110a-110f is not filled, for example, FIG. 4, which will be discussed later, depicts this type of ultrasound transducer.

Returning to FIG. 1, filling space 140a-140e between each two of the piezoelectric elements 110a-110f provides at least four advantages.

Figure 18:
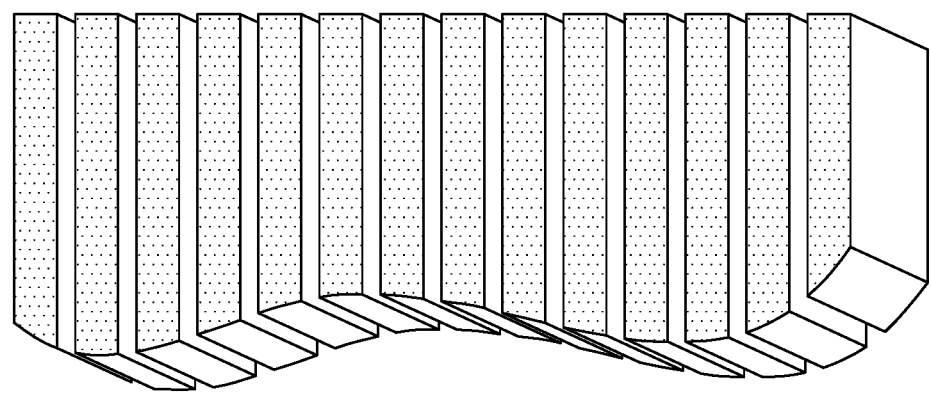
FIG. 18 depicts an example of piezoelectric elements that can be utilized in an embodiment of the present invention.

First, filling the spaces 140a-140e with a material can bond the piezoelectric elements 110a-110f together separately from electrical connections. The bonding of the piezoelectric elements 110a-110f enables the stack formed from the piezoelectric elements 110a-110f to be machined into various shapes. Embodiments of the transducer structure and electrode configuration in this invention allow for machining of the acoustic transmitting surfaces both before and after fabrication. This flexibility provides for mechanical focusing and acoustic beam shaping. The various stack configurations of elements of similar and/or varied transverse resonance of embodiments of the present invention allow the transducer to be broad-band in its frequency sensitivity and designed into arbitrary shapes while maintaining low-voltage drive capability. An example of such a shape is seen in FIG. 18. In an embodiment of the present invention, when a stack is machined to a desired shape, after machining, the transducer will have an equivalent impendence at a higher frequency when compared to the transducer prior to machining. When a lens is included in the transducer, the stack, the lens, and the combination of the machine and the stack can all be machined.

Second, filling the spaces 140a-140e may improve the heat transfer characteristics of the transducer.

Third, filling the spaces 140a-140e reduces acoustic cross-talk and potentially reduces electrical cross-talk. Specifically, acoustic cross-talk is reduced by the presence of filler material, while electrical cross-talk is reduced if the filler material is electrically insulating. Electrical cross-talk is also reduced by the fact that similar polarities of the piezoelectric elements are adjacent to each other.

Finally, filling the spaces 140a-140e may increase the ultrasonic performance and durability of the transducer, to prevent shock from dropping, heat expansion, and general wear, as opposed to piezoelectric elements that are floating in air, which act like cantilever arms and are susceptible to thermal expansion and mechanical damage. Thus, securing the components of the transducer improves the durability of the transducer.

The variety of transducer configurations is advantageous, for example, in the operation of the transducer in portable electronic applications, where impedance should be minimized and voltage to acoustic pressure conversion maximized, and in electronic focusing of arrays where driver electronic cross talk needs to be minimized.

Figure 5:
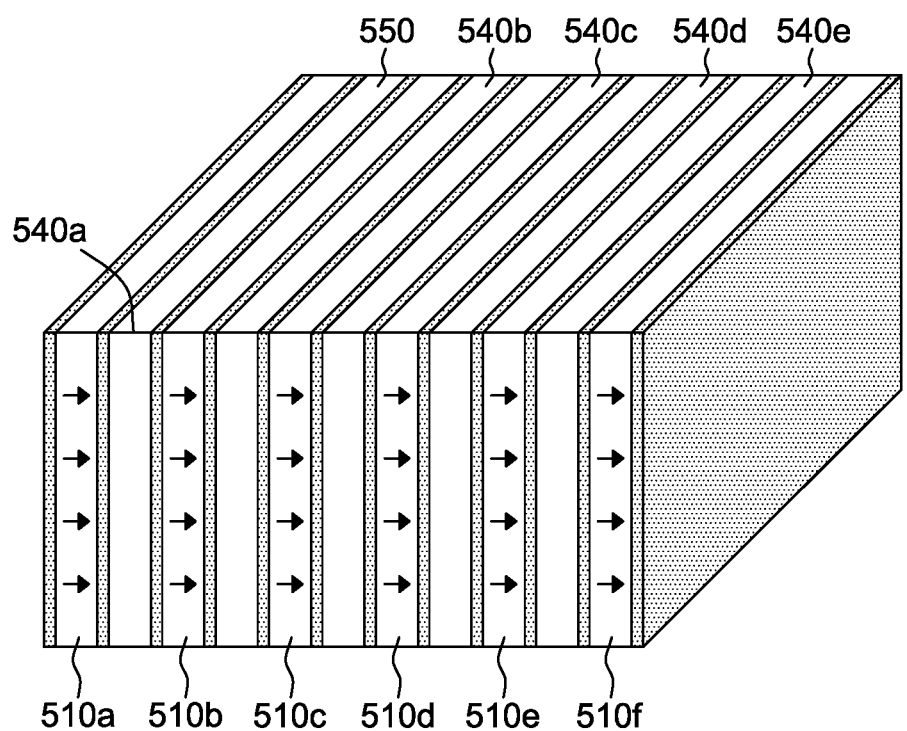
FIG. 5 depicts aspects of an embodiment of the present invention.
Figure 10:
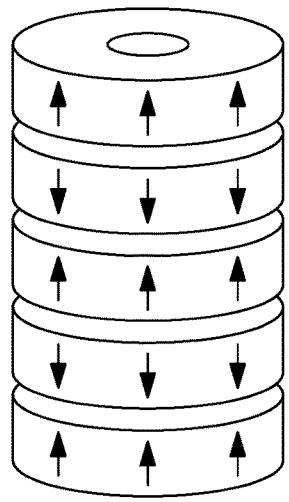
FIG. 10 depicts aspects of a configuration of piezoelectric elements utilized in an embodiment of the present invention.

FIG. 5 depicts certain elements of the transducer of FIG. 1, including the piezoelectric elements 510a-510f and the spaces 540a-540e in-between these elements. In this embodiment, an ultrasound transducer is formed from laminations of piezoelectric ceramic and polymer materials. In another aspect, the present invention relates to a transverse mode 1-3 composite ultrasound transducer comprised of a plurality of bi-laminated oppositely poled piezoelectric ceramic elements. FIG. 10 demonstrates a similar staking approach for piezoelectric elements that are disks (rings).

When combining piezoelectric elements that are disks into a transducer, individual stacks can be segregated from each other in embodiments of the present invention. For example, each of a group of stacks can be sealed, individually, in an epoxy housing and wired in parallel to a low impedance coaxial cable.

Returning to FIG. 5, the piezoelectric elements 510a-510f, which in this example are piezoelectric ceramics, are connected over the spaces 540a-540e with a polymer filling 550. In embodiments of the present invention, this filling can be any of a variety of filled and unfilled materials such as epoxy, polyurethane, silicone, thermal conductive material, electrically conductive material, fluid, and/or a vacuum. Some of these in turn can be filled with materials such as micro-bubbles, heat transfer substances absorbing rubbers etc., substances that can be used to enhance the functionality of the composite in specific applications. In a non-limiting example of an embodiment of the present invention, in designing a transducer that would be used to transmit into air, an epoxy filled with micro-bubbles is utilized as the polymer filling 550. Air has very low acoustic impedance compared to piezoelectric ceramics.

In composite transducers, such as those depicted in the figures, in accordance with the techniques of the present invention, polymer filler can be chosen to lower the acoustic impedance of the overall transducer providing improved acoustic impedance matching to the air. Micro-bubbles which are thin spheres filled with air, when mixed with polymers; provide a low acoustic impedance filler material.

FIG. 5 further illustrates the stacking of the individual piezoelectric elements 510a-510f, to form a block of transverse mode composite material. The individual segments can be bonded together by any number of low viscosity adhesives to form the block. As can be understood by one of skill in the art, the center electrodes of the individual segments may be brought out to the side of the composite where they can be joined together to form a single conductor, or left separated to form individual addressable elements that can be used in electronic focusing. These electronic properties can be achieved by using wires, flexible circuit boards or other electrical conductivity methods known to one of skill in the art. The direction of propagation for an acoustic wave-front is normal to the transmitting surface. The back side of the composite is where the outside electrodes of the individual segments are brought to the back side. These electrodes can be tied together to form a common return path, or left as individual return paths for improved cross coupling performance.

A variety of techniques can be utilized to apply the selected polymer filling 550 to the piezoelectric elements 510a-510f and the spaces 540a-540e. For example, the polymer material can be formed to a thickness of the same length as the distance between the piezoelectric elements and then glued to the sides of adjacent elements to fill the space between them. Alternatively, the polymer can be poured over the stack and lapped the polymer from the transmitting (non-electrode) sides of the piezoelectric elements.

In an embodiment of the present invention, the polymer is ½ the thickness of the final composite filler thickness. For example, for a 225 KHz transducer with 50% volume fraction this layer is approximately 0.101 mm thick.

Figure 6:
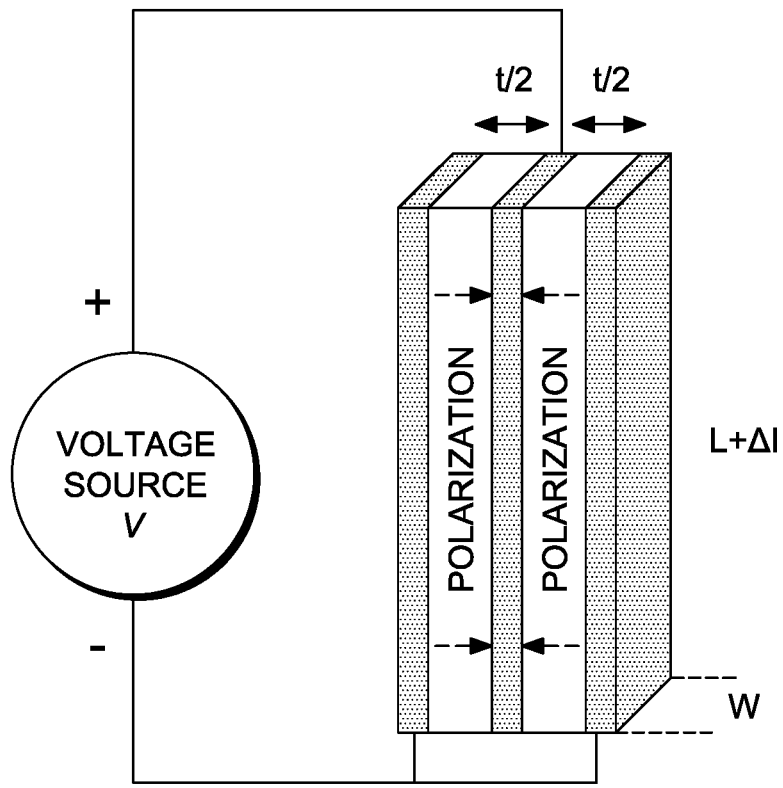
FIG. 6 depicts a stacked piezoelectric element used in an embodiment of this invention.

Returning to FIG. 1, the spaces 140a-140e between piezoelectric elements 110a-110f can vary. In some embodiments of the present invention, these spaces 120a-120e are delineated by epoxy, which is utilized to bond the electrodes of the piezoelectric elements 110a-110f together. The epoxy does not enable an electrical connection between the electrodes, merely, a mechanical connection. FIG. 6 depicts portions of a transducer, specifically, two piezoelectric elements 610a-610b, which are plates, in this example, bonded together. The two piezoelectric elements 610a-610b (plates) are bonded together by aligning the exposed electrode sides adjacent to each other along their entire lengths and gluing with a low viscosity adhesive such as a cyano-acrylic, forming a sandwich of piezoelectric composite material between outer polymer and with a set of inner and outer electrodes.

Figure 7:
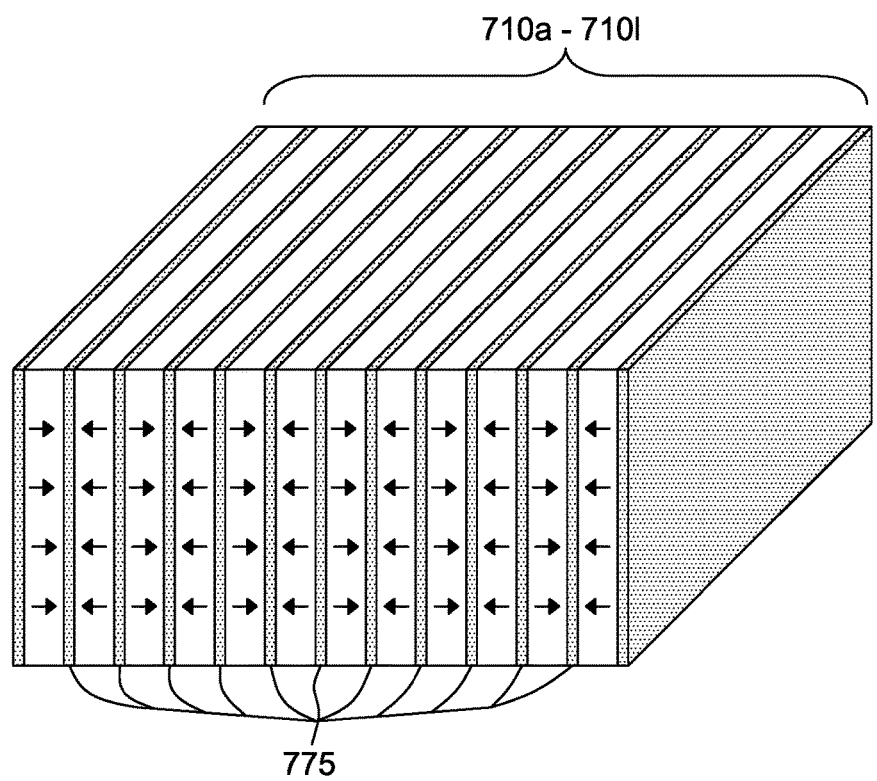
FIG. 7 depicts a configurations of piezoelectric elements utilized in an embodiment of the present invention.

FIG. 7, like FIG. 6, shows a bonding of piezoelectric elements 710a-7101 with a glue 775, including but not limited to, a heat resistant epoxy. In the configuration in FIG. 7, electrodes with like polarity are bonded to the epoxy so that they face each other in the stack. In FIG. 7, the piezoelectric elements 710a-7101, which can be, for example, ceramic plates, are stacked in parallel along its length at regular pre-determined intervals. In an embodiment of the present invention, the spacing and thickness of these parallel piezoelectric elements 710a-7101 may be based upon the volume fraction of ceramic material in the final transducer structure. In one non-limiting example, in fabricating a transducer with a 225 kHz height. With a 1650

Hz-meters transverse length frequency constant for PZT4, the length is 7.33 mm. Then, with a 30:1 ratio of length to thickness, the element thickness is 0.488 mm. With 50% volume fraction, the space thickness should be half of the element, thickness which is 0.244 mm.

As aforementioned, in embodiments of the present invention, once piezoelectric elements are bonded together, the stack can be machined. Referring the FIG. 18, this post-fabrication machining of piezoelectric elements is possible in part because the electrodes of the elements are not on the surfaces of the piezoelectric elements that are emitting ultrasound. Rather, ultrasound is emitted from a bottom surface 1895. Further, wires (not pictured) that couple the electrodes of the piezoelectric elements together can be found on a top surface 1897, opposite the acoustic transmitting surfaces). Therefore, after adding a filler, including but not limited to, epoxy, to a transducer stack, the bottom 1895 can be cut and shaped without affecting the coupling wires or the ultrasound transmitting face.

In an embodiment of the present invention, a transducer maintains an aspect ratio for the individual piezoelectric elements, such that the height to thickness ratio is greater than 3 to 1. This provides for a low impedance configuration and an increase in low-voltage drive capabilities over existing prior art transducers.

Figure 8:
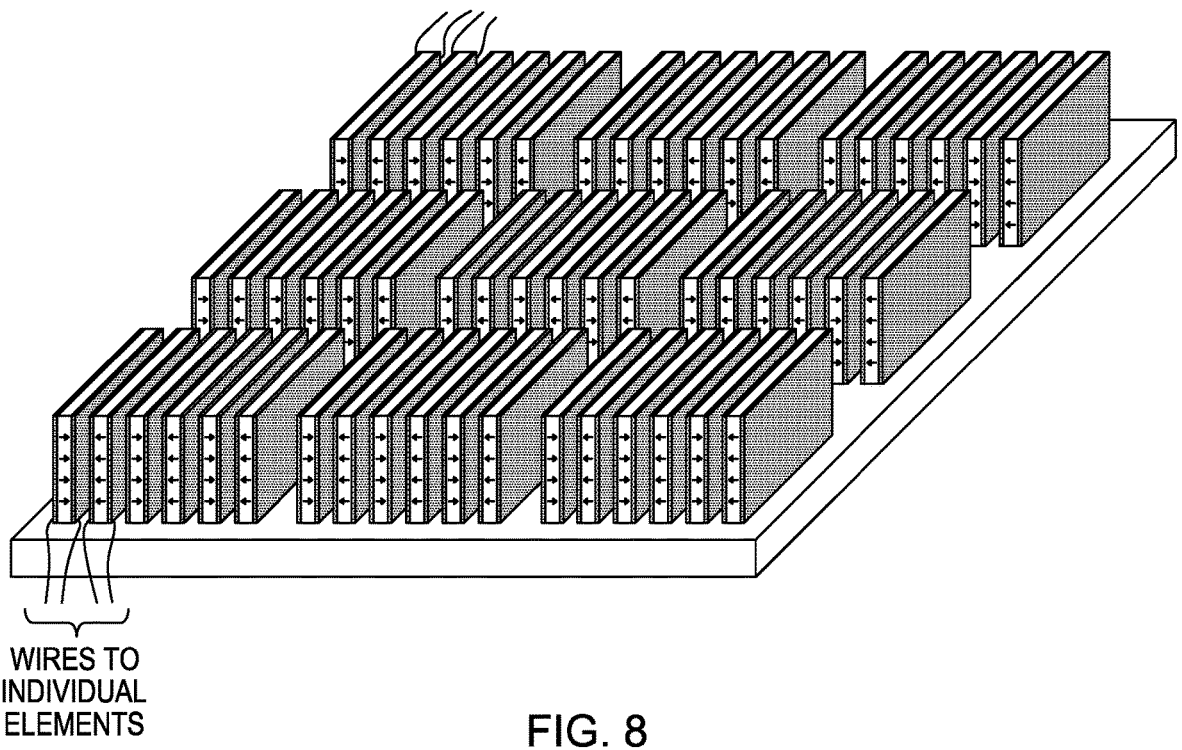
FIG. 8 depicts certain details of an electronic configuration of an embodiment of the present invention.

In embodiments of the present invention, plates can be electronically steered by driving individual piezoelectric elements, separately, and/or by driving groups of piezoelectric elements, together. As seen in FIG. 8, the piezoelectric elements 810a-810f in this embodiment of an ultrasound transducer of the present invention can be driven separately. Additionally, the piezoelectric elements may be made of different materials and operate at different frequencies.

Figure 9:
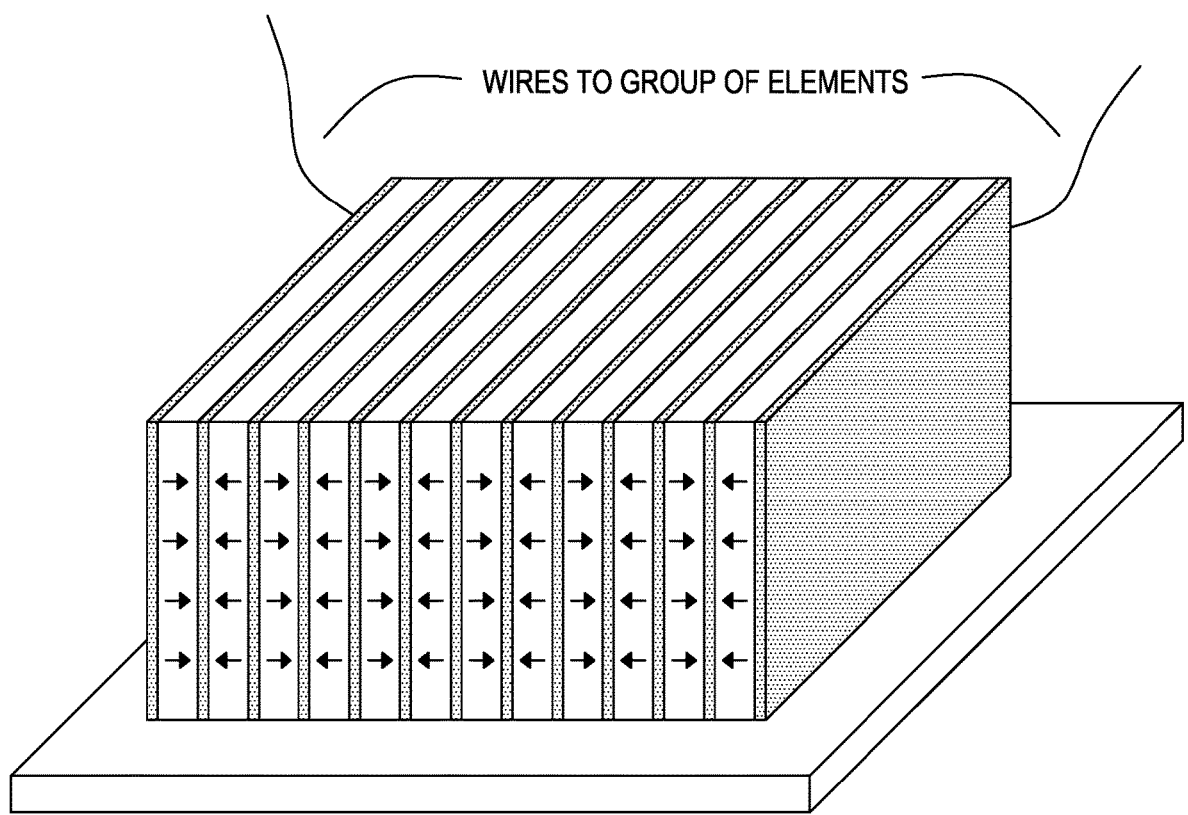
FIG. 9 depicts certain details of an electronic configuration of an embodiment of the present invention.

To accomplish this, the piezoelectric elements 810a-810f are situated in an array configuration (i.e., electrodes on the non-articulating sides), so an individual element can be driven to generate a low-frequency signal. As seen in FIG. 9, the piezoelectric elements 910a-910f are driven in a group of 1 or more elements. The geometry of these elements enables them to be grouped together to generate a low-impedance input. In the embodiments similar to FIG. 9, two or more thin elements can be grouped together to act as a single channel. Utilizing the teachings of the present invention, in the embodiment of FIG. 8, a number of element stacks, for example, 14 element stacks, can be individual channels and placed in a transducer array. But utilizing the teachings of embodiments such as FIG. 9, a quantity of elements can be stacked, for example 80 elements, and two such stacks (of multiple elements) can be placed in a transducer housing and wired in groups of for example, ten elements, to create, for example, a 16-channel array.

In an embodiment of the present invention, a transducer can be configured so that individual stacks of piezoelectric elements in the transducer fire independently. Stacks can be configured in a linear array. As the frequency is increased the power density and divergence of the ultrasound beam is increased and reduced, respectively.

Figure 4:
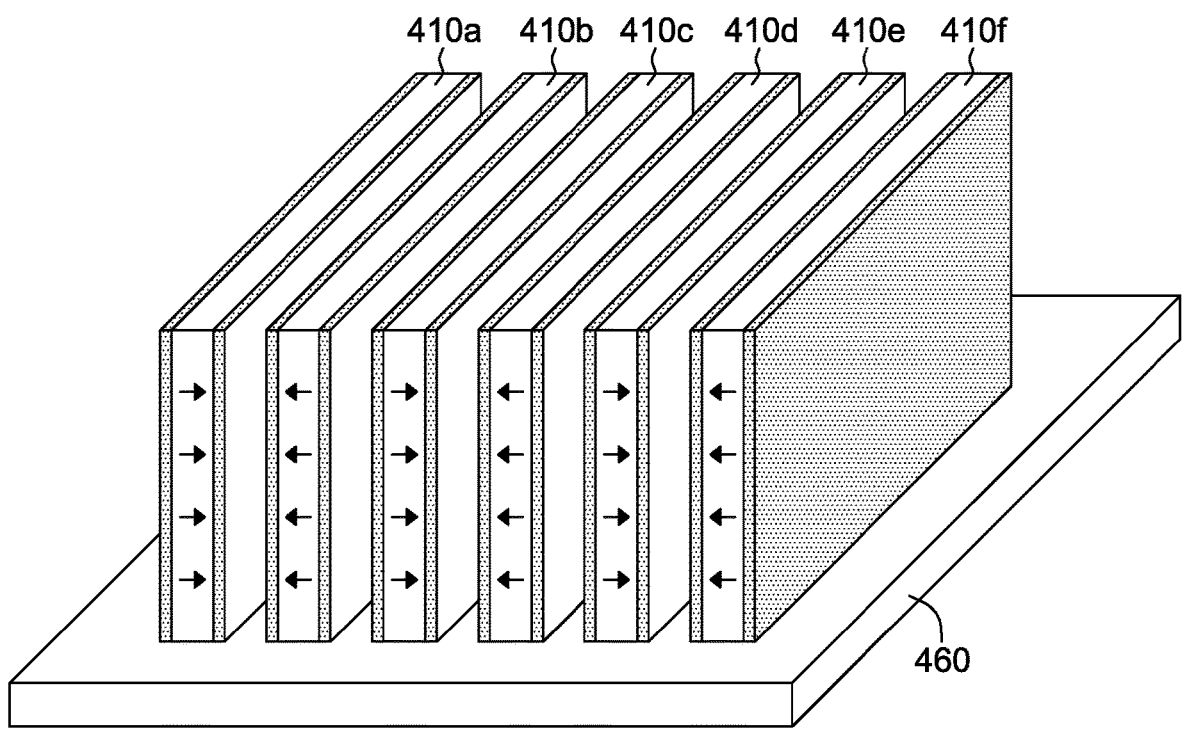
FIG. 4 depicts aspects of a configuration of a parallel piezoelectric stack transducer of the present invention.

As seen in FIG. 4, an embodiment of the transducer of the present invention can also include a lens 460. The lens can include an upper surface 465, and a bottom surface 462a-462f of each of the piezoelectric elements 410a-410f is coupled to the upper surface 465 of the lens 460. This configuration maintains the parallel and stacked placement of the piezoelectric elements 410a-410f in the ultrasonic transducer. In embodiments of the present invention, the lens 460, can be contoured to focus, diverge, and/or direct, ultrasound.

In an embodiment of the present invention, the transducer can also be coupled to a matching layer for improved acoustic transmission or acoustic receiving.

In embodiments where the piezoelectric elements are ceramics, the electrodes are on the sides and the bottom is coupled to a lens. The shape of the piezoelectric ceramics determines excitation frequency at different resonances (i.e., thickness mode, radial mode, length mode). In an embodiment of the present invention, in a stack transducer, one of the ceramics that is utilized is a length-wise resonator. Thus, in FIG. 4, the bottom surface that is coupled to the lens and that is emitting the ultrasound is not an electrode. The electrodes of the piezoelectric elements are located on the sides of the ceramic and not on the face that is transmitting the acoustic signal. The lens can be contoured to focus, diverge, and/or direct, ultrasound.

For embodiments of the invention that include a lens, methods of making this transducer include machining a lens to a pre-defined contour suitable for focusing, diverging, or directing, ultrasound. In some embodiments of the present invention that include a lens, wiring (not pictured) utilized to electrically connect the piezoelectric elements 410a-410f, are positioned such that they do not come into contact with the lens 460. Thus, the stack that includes the piezoelectric elements 410a-410f and the filler can be machined to fit on the contours of the lens without affecting the electrical connectivity of the individual elements.

Figure 11:
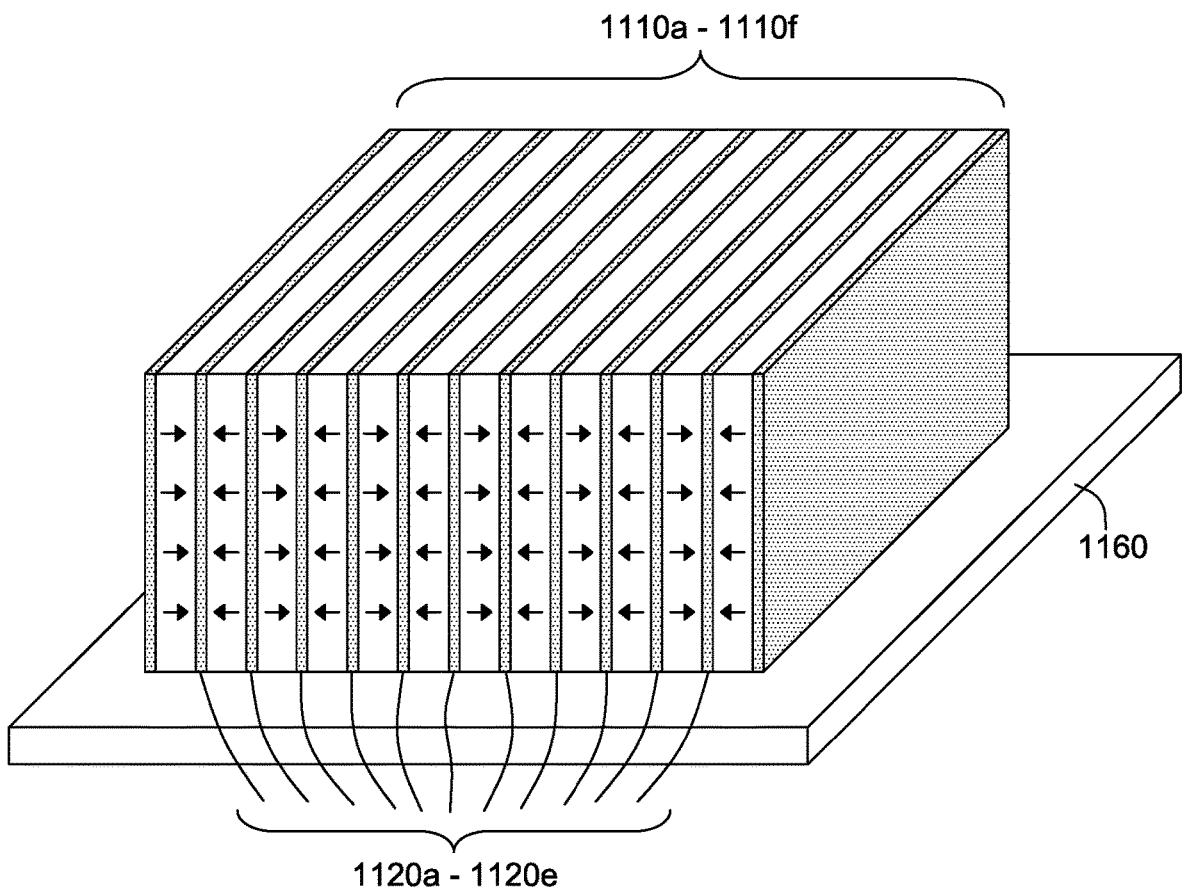
FIG. 11 depicts aspects of an embodiment of the present invention.

Like FIG. 4, FIG. 11 also depicts aspects of an embodiment of the present invention that includes a lens 1160. However, in this embodiment, filler material comprises the spaces between the piezoelectric elements 1110a-1110f are spaces 1120a-1120e that are filled with a material, for example, a polymer matrix.

In embodiments of the present invention, the lens may be an epoxy, plastic, metal, resin or a like material as recognized by one of skill in the art. As aforementioned, the lens may be machined to any contour for focusing, directing and/or diverging the ultrasound. The lens may be machined down to and/or into the piezoelectric stack itself.

Figure 17:
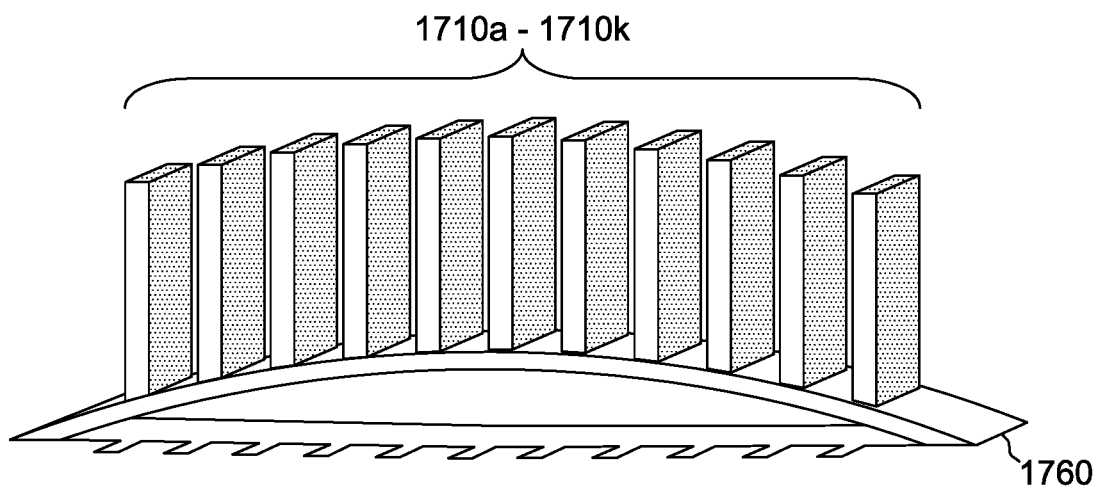
FIG. 17 depicts aspects of an embodiment of the present invention.

FIG. 17 depicts aspects of an embodiment of the present invention where the lens 1760 to which the piezoelectric elements 1710a-1710k are affixed is not a plane. As discussed earlier, lenses in transducers of the present invention can be contoured to focus, direct and/or diverge the ultrasound. In the embodiment of FIG. 17, the radius of the curved surface of lens 1769 creates a natural focus. In this embodiment, the piezoelectric elements 1710a-1710k are coupled to this curved surface and wired (not pictured) in parallel. The stack is mechanically focused by the curved surface, so when the piezoelectric elements 1710a-1710k are stimulated at the same time, the acoustic signals will focus (i.e. reach a max acoustic pressure) based on the curvature of the surface of the lens 1760.

An embodiment of the present invention utilizes an array of stack transducers and affixes these arrays to a curved surface, like the lens 1760 of FIG. 17. In this configuration, each stack transducer may act as a point source of energy on this curved surface and will create a mechanical focus if all stack transducers are driven simultaneously.

Figure 12:
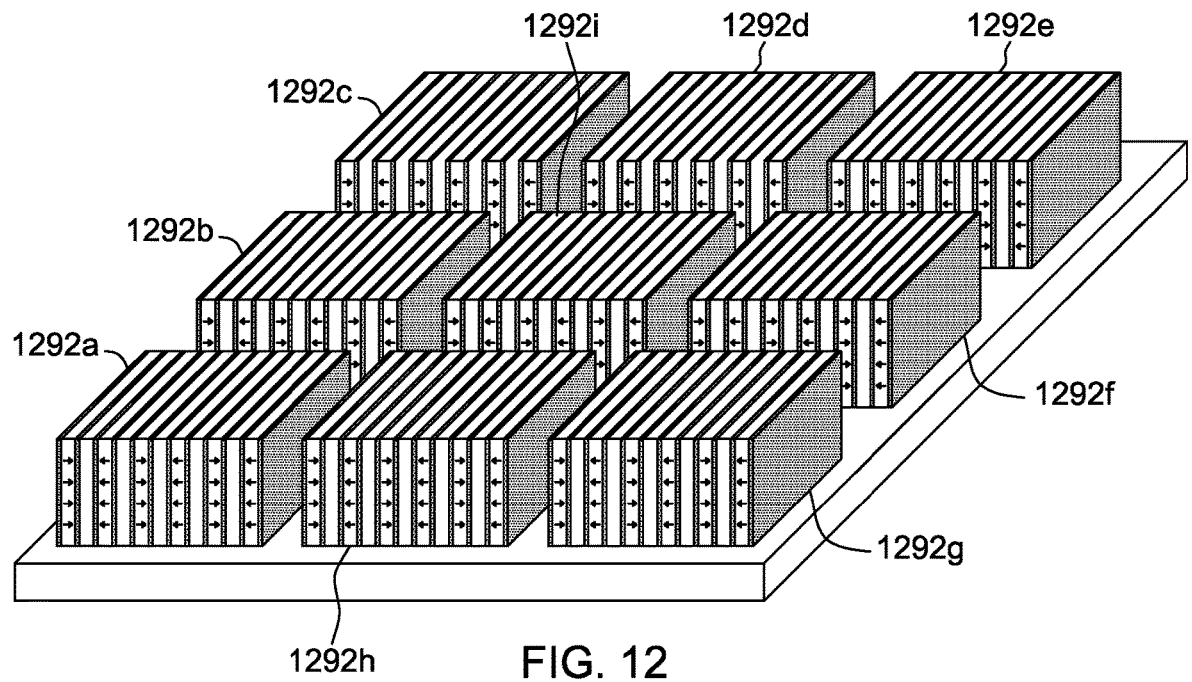
FIG. 12 depicts an array configuration utilized by an embodiment of the present invention.
Figure 13:
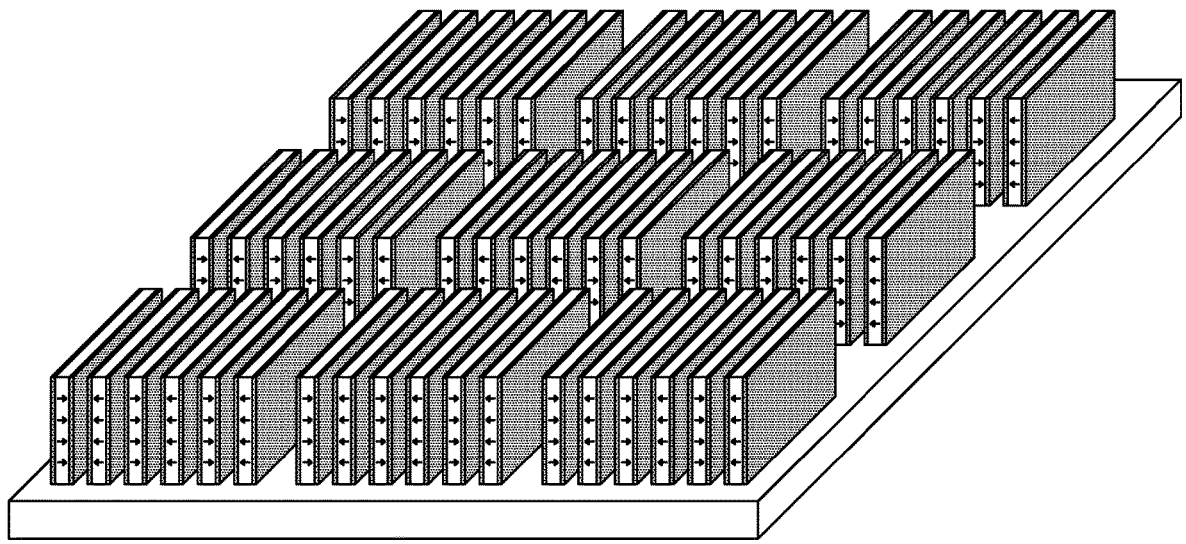
FIG. 13 depicts an array configuration utilized by an embodiment of the present invention.

The orientations of the stacks of piezoelectric elements are not limited to those depicted in the figures. Embodiments of the present invention include various configurations of parallel piezoelectric stack transducers in various configurations on low-profile lens and transducer front face material including, but not limited to: linear array, mechanically focused, single channel and 2D array, and 3D low-frequency and low-profile ultrasound transducer arrays. FIG. 12 and FIG. 13 provide some additional examples of configurations. In various embodiments of the present invention, individual stacks of piezoelectric elements may be configured into variable orientations for directing ultrasound in preferred directions in 2D and 3D arrangements Referring the FIG. 12, the embodiment depicted is a two dimensional (2D) array configuration of parallel piezoelectric stacks 1292a-1292i on a low-profile lens 1260 and transducer front face material 1262. In this embodiment, the stacks 1292a-1292i may be electronically driven together, or independently. Additionally, the individual piezoelectric elements of each stack 1292a-1292i may also be driven together or independently. This described functionality (driving individual stacks and elements together) is also enabled in the embodiment of FIG. 13, which is also a 2D array configuration.

Figure 23:
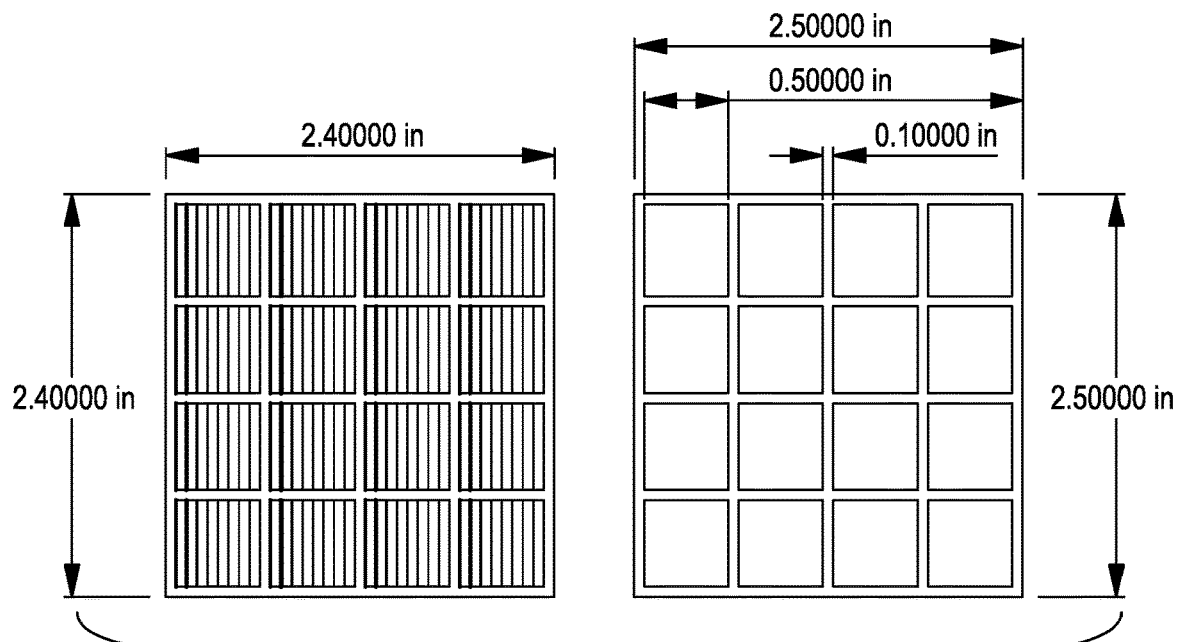
FIG. 23 depicts aspects of an embodiment of the present invention.

FIG. 23 depicts an embodiment with a 2D array configuration of piezoelectric stacks for a multi-channel low frequency and low impedance transducer. The measurements provided in this figure are offered by way of example and are not limiting.

FIG. 24 depicts another embodiment of the transducer of the present invention specifically, a linear configuration of eight, 10-element piezo-ceramic stacks sharing a common ground. The group of stacks is aligned with side spacers running the length of the array. Electrical connections are made on the top corners of the individual piezo elements, as shown in FIG. 24 with boxes around these elements.

Embodiments of the present invention can be secured inside housings and/or electrically connected to external electronic components. In an embodiment of the present invention, a polystyrene housing positions and aligns the piezoelectric elements. In an embodiment of the present invention, the piezoelectric elements of the present invention are secured within a polystyrene housing with a cyano acrylic glue—individual piezoelectric elements can be electrically grouped. In a further embodiment of the present invention, more than one transducer can be attached to a low-impedance coaxial cable. In an embodiment of the present invention, an array, such as an either channel array, may be placed into a polystyrene and ABS housing, with multi-conductor shielded cable wiring with shared ground. In embodiments of the present invention, though channels share a common ground, independent signal channels may be provided by shielded multi conductor cable.

Orientations of piezoelectric elements in housings can vary between embodiments. In one embodiment of the present invention two, sixteen, 10-element piezo-stack arrays are placed side-by-side and housed in polystyrene and ABS housing. The channels in this embodiment share a common ground, with independent signal channels provided by shielded multi conductor cable. Alternatively, each element may be secured to a polystyrene face plate with build in spacers. Another embodiment includes a high density packed transverse piezoelectric stack actuator composed of 10 elements with aluminum ribbon conductors interleaved between element layers providing electrical conductivity.

Figure 14:
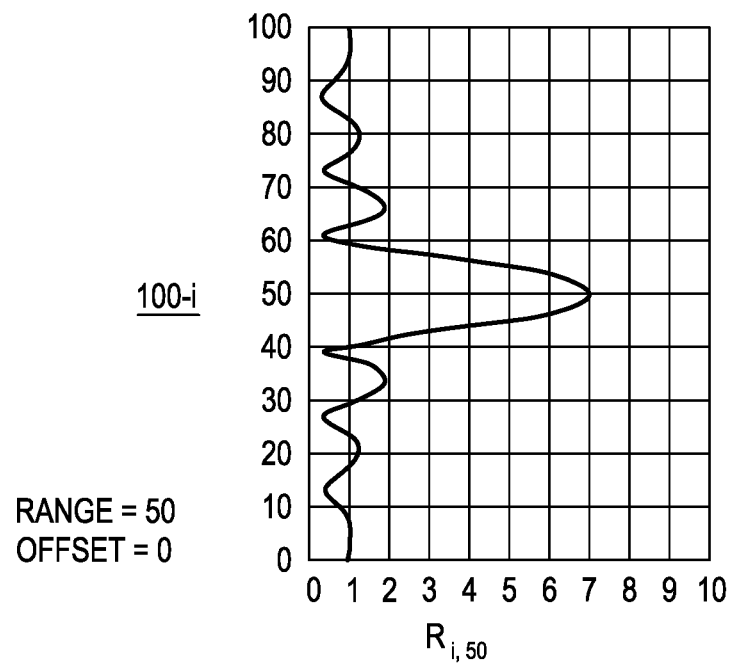
FIG. 14 demonstrates the focusing capabilities of an embodiment of the present invention.
Figure 14:
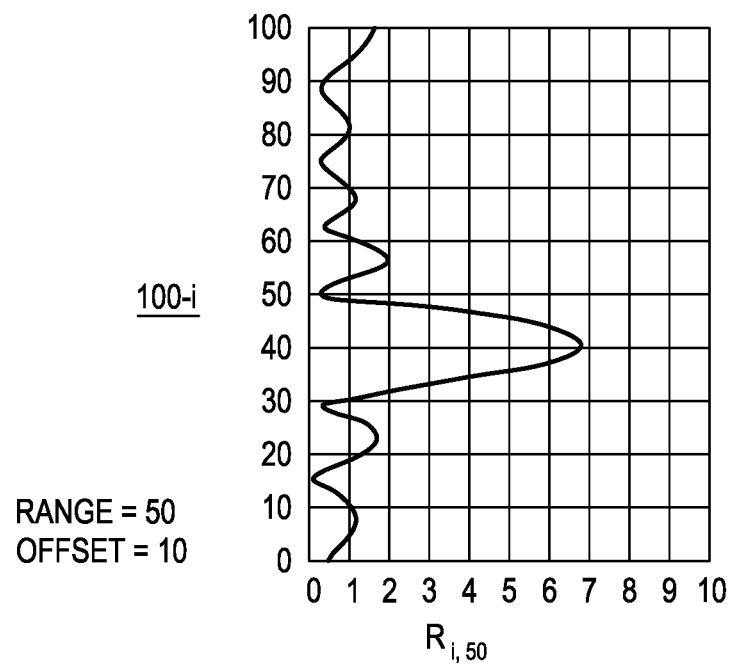
Figure 15:
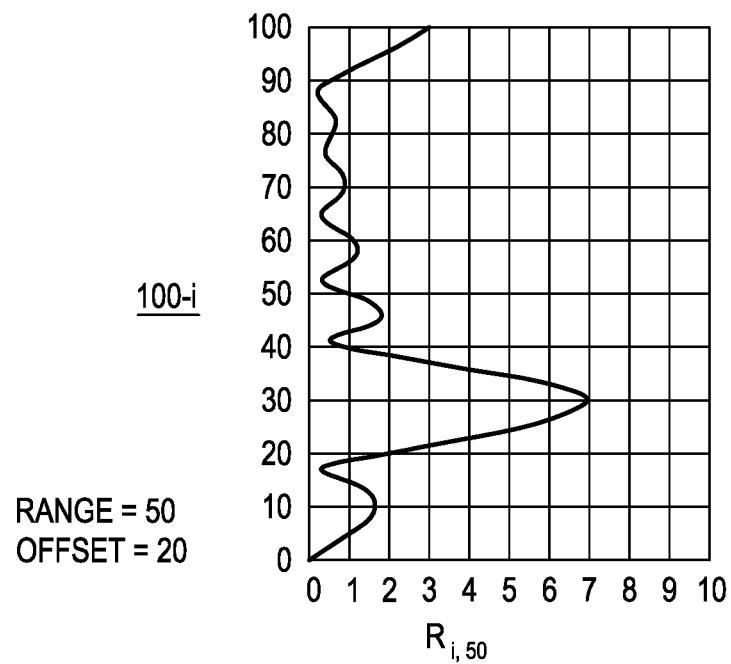
FIG. 15 demonstrates the focusing capabilities of an embodiment of the present invention.
Figure 15:
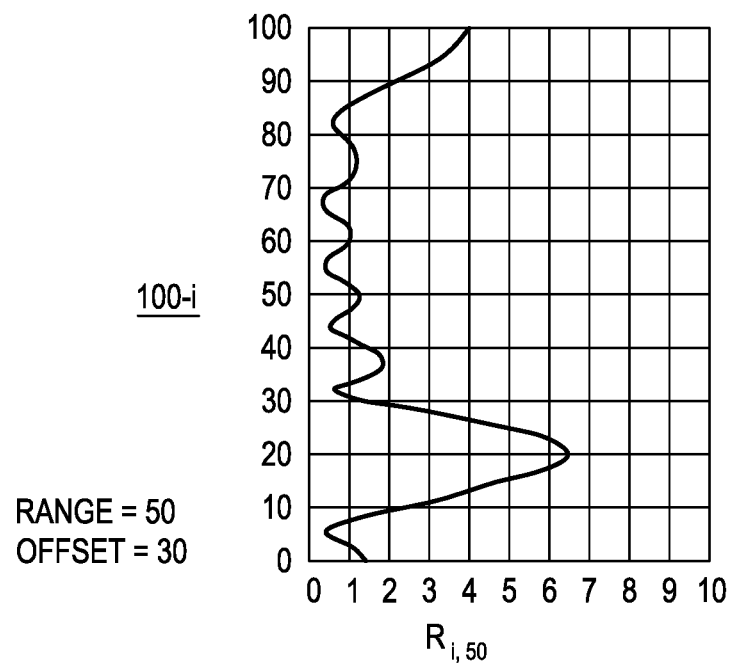
Figure 16:
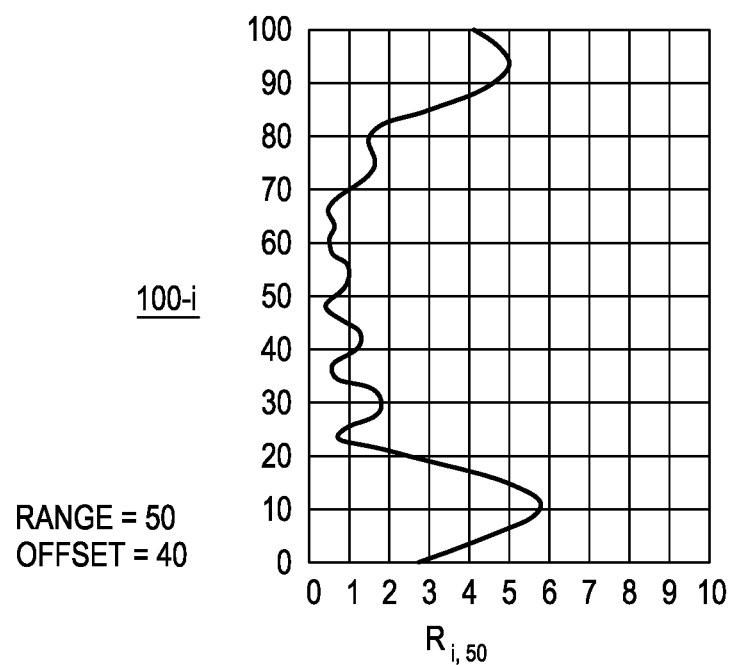
FIG. 16 demonstrates the focusing capabilities of an embodiment of the present invention.

As an example, FIGS. 14-16 illustrate dithering the focal zone of a seven 10 element stack of a low impedance low frequency array, as constructed in accordance with the present invention. To get an understanding of the range of distance that the acoustic beam can be steered, the model takes into account a couple of variables, Range and Offset. Range is the horizontal distance from the front of the transducer to the focal point while Offset is the vertical distance perpendicular to the center of the transducer axis. From the figures one can see that it is easy to phase the seven stacks to move the focal point greater than 1" (25 mm) on either side of the transducer axis.

Figure 19:
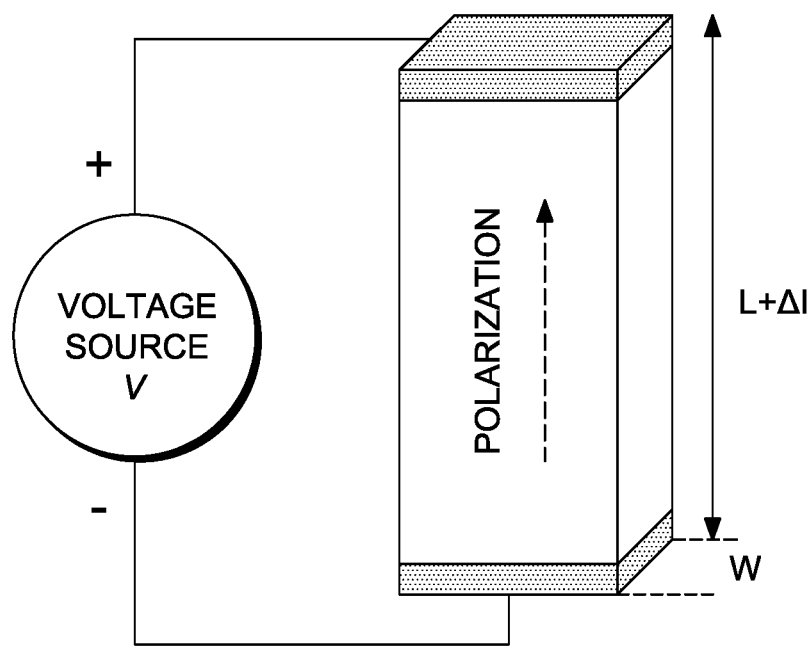
FIG. 19 depicts an example of a piezoelectric element.
Figure 20:
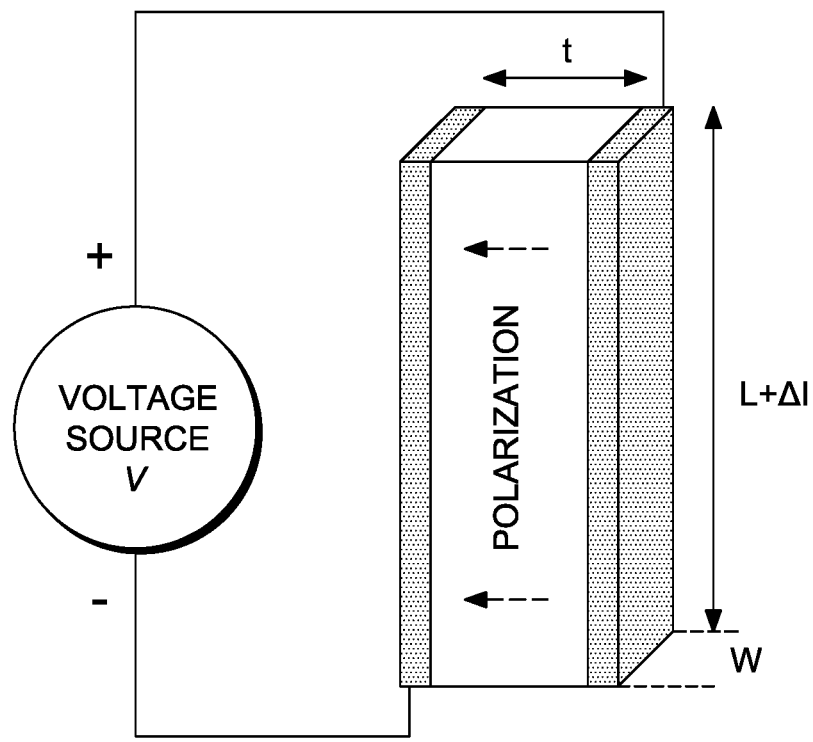
FIG. 20 depicts an example of a piezoelectric element.

FIGS. 19, 20 and 6 illustrate some of the advantages of the present invention over ultrasound transducer that were previously utilized.

FIG. 19 depicts piezoelectric element 1910, a ceramic plate. This piezoelectric element 1910, which is polarized in the length direction, has electrodes on the short ends of the ceramic normal to the poling direction. This is referred to as the longitudinal mode of transducer operation. When a voltage is applied to this ceramic its length will change according to the relation of Equation 1 below, $\Delta L_{longitudinal}/L$.

$$\frac{\Delta l_{longitudinal}}{L} = d_{33} \cdot \frac{V}{L} \qquad \text{Equation 1}$$

FIG. 20 illustrates another piezoelectric element 2010 which is polarized in the thickness direction and has electrodes on the long sides of the ceramic also normal to the direction of poling. This is referred to as the transverse mode of transducer operation. When a voltage is applied to the electrodes on this ceramic its length will change according to the relation represented by Equation 2 below.

The constants $d_{33}$ and $d_{31}$ are physical parameters of the piezoelectric ceramic material and relate the strain in the ceramic to the applied electric field. For a large majority of piezoelectric ceramic material the transverse constant $d_{31}$ is about ⅓ the value of $d_{33}$. Because of this in order to obtain the same amount of strain in the length direction for the same applied voltage the thickness of ceramic in the transverse mode should be made less than ⅓ of its height.

$$\frac{\Delta l_{longitudinal}}{L} = d_{31} \cdot \frac{V}{t} \qquad \text{Equation 2}$$

Per the above, $\Delta L_{longitudinal}/L$, and returning to FIG. 6, this figure, as aforementioned, illustrates a stacked piezoelectric element used in an embodiment of the present invention. In this example, two tall thin piezoelectric elements 610a-610b operating in transverse mode are sandwiched together such that the inner electrode is common to both ceramics. The outer electrodes are chosen so that the polarization internal to the two ceramics opposes each other. When a voltage is applied between the outer and inner electrodes both ceramics will change length in the same direction according to Equation 3, below.

$$\frac{\Delta l_{sandwich}}{L} = 2d_{31} \cdot \frac{V}{t} \qquad \text{Equation 3}$$

Per the above, $\Delta L_{sandwich}/L$, for a transducer operating at a frequency of 225 KHz and using a PZT4 or PZT8 type piezoelectric ceramic with a transverse length frequency constant of 1650 Hz-meters, the length (L) would be 7.33 mm. For a 10:1 or 30:1 ratio of length to thickness in each individual element the thickness of the sandwiched should be 1.47 mm and 0.488 mm, respectively. The gain in displacement of the sandwiched element as embodied in this invention over a longitudinal element represented by Equation 4, below. This discussed earlier in relation to various embodiments of the present invention, $$\text{Gain} = \frac{\Delta l_{sandwich}}{\Delta l_{longitudinal}} = 2\frac{d_{31}}{d_{33}} \cdot \frac{L}{t} \qquad \text{Equation 4}$$

As noted in the equation, gain is $\Delta L_{sandwich}/\Delta L_{longitudinal}$. Thus, For PZT4/8 type piezoelectric ceramic $d_{33}=270$ and $d_{31}=-120$. Using the values one can calculate the magnitude of the Gain to be 4.44 and 13.33 for 10:1 and 30:1 length to thickness ratios, respectively. Thus the parallel transverse mode element in this invention will yield over more displacement when compared to previously known techniques utilizing longitudinal mode element of equivalent dimensions and applied voltage.

It should be pointed out that this gain in displacement does not come for free. Although the drive voltages are the same, the amount of charge or current will be substantially larger. This is a direct result of the increased capacitance and lower impedance for the thin piezoelectric transverse element which has electrodes over a more extensive surface area compared to the smaller and further separated electrodes in the longitudinal element.

Furthermore, the $d_{31}$ constant is a negative number. This arises because when a positive voltage is applied in the direction of poling it causes the ceramic to expand in that direction. Because of Poisson's ratio, expansion in the transverse direction will cause contraction in the longitudinal direction.

Figure 21:
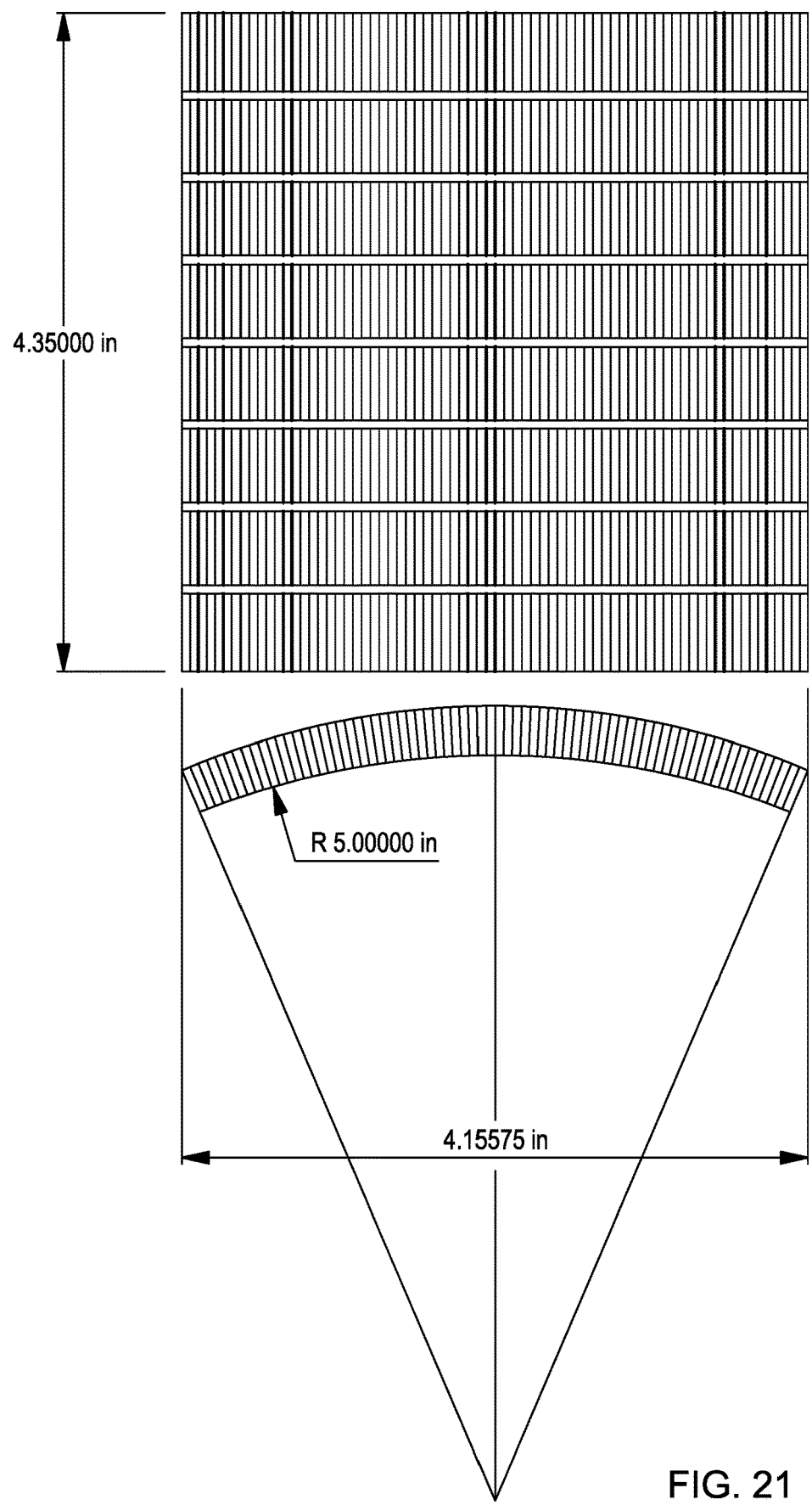
FIG. 21 depicts aspects of an embodiment of the present invention.
Figure 22:
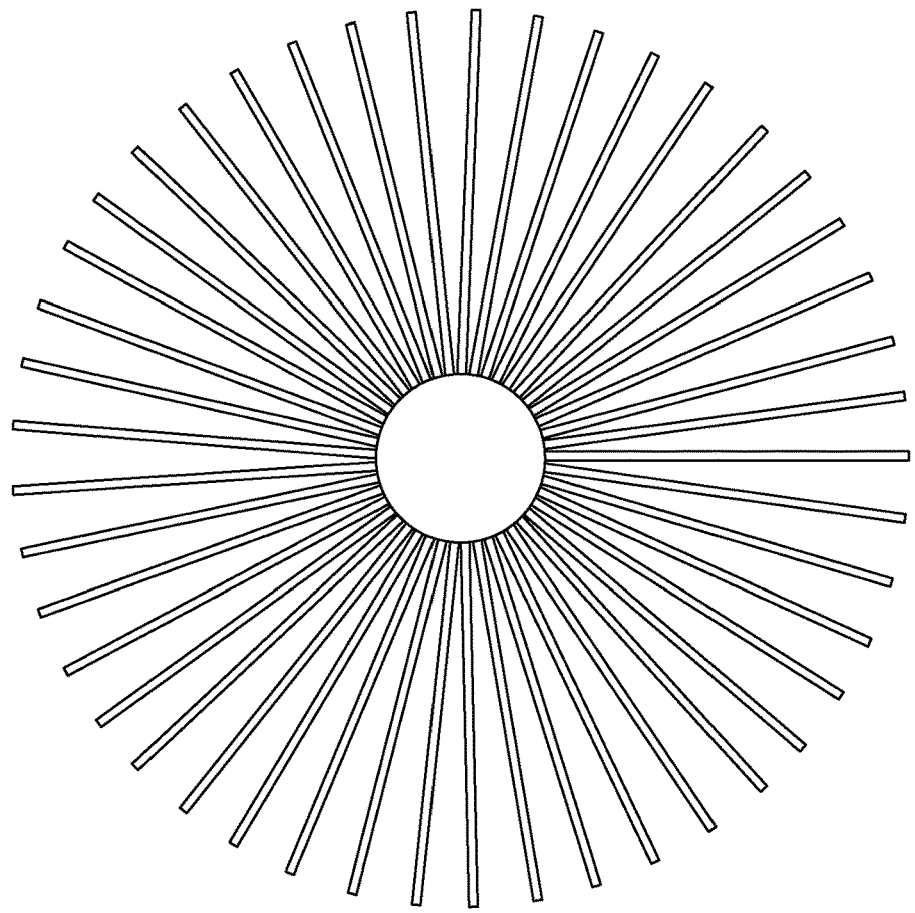
FIG. 22 depicts aspects of an embodiment of the present invention.

As discussed earlier, a variety of configurations of piezoelectric elements can be utilized in different embodiments of the present invention. FIG. 21 depicts an embodiment of the present invention where an ultrasound transducer is made utilizing a cylindrical (e.g., 5 in) focused piezoelectric stack array that may be mounted onto a front face material. FIG. 22 is another embodiment where a circular fan-out configuration of a parallel piezoelectric stacks form aspects of an ultrasound transducer.

Various aspects and embodiments of the present invention can be used with other portable ultrasound systems and low-profile ultrasound transducers, including, without limitation, those disclosed in U.S. Provisional Patent Application No. 61/838,773, U.S. Provisional Patent Application No. 61/838,811, both filed on Jun. 24, 2013, and International Application No. PCT/US2014/043953, entitled "WEARABLE ULTRASOUND DEVICE," filed on Jun. 24, 2014.

While several aspects of the present invention have been described and depicted herein, alternative aspects may be affected by those skilled in the art to accomplish the same objectives. Accordingly, it is intended by the appended claims to cover all such alternative aspects as fall within the true spirit and scope of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the descriptions below, if any, are intended to include any structure, material, or act for performing the function in combination with other elements as specifically noted. The description of the technique has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An ultrasound transducer, comprising:
   at least two piezoelectric elements, oriented adjacent to each other in a stack, wherein each of the at least two piezoelectric elements comprises:
      a first side surface comprising an electrode of a first polarity;
      a second side surface comprising an electrode of a second polarity; and
      an ultrasound transmitting surface having a smaller surface area than the surface area of each of the first and second side surfaces;
   a first electrical connection between a surface of a first of the at least two piezoelectric elements of the first polarity and a surface of a second of the at least two piezoelectric elements of the first polarity; and
   a second electrical connection between a surface of a first of the at least two piezoelectric elements of the second polarity and a surface of a second of the at least two piezoelectric elements of the second polarity,
   wherein the at least two piezoelectric elements are oriented adjacent to each other when an entire electrode surface of the first of the at least two piezoelectric elements is adjacent to an entire electrode surface of the second of the at least two piezoelectric elements.

2. The transducer of claim 1, wherein the stack of the transducer is of a pre-determined thickness, and wherein an electrical impedance of the transducer is less than an electrical impendence of a second transducer, the second transducer comprising one piezoelectric element of the pre-determined thickness.

3. The transducer of claim 1, wherein a height of at least one of the two piezoelectric elements is at least three times greater than a thickness of the at least one of the two piezoelectric elements.

4. The transducer of claim 1, wherein in the stack, an electrode of a first polarity of a first piezoelectric element of the at least two piezoelectric elements is positioned adjacent to an electrode of a second polarity of a second piezoelectric element of the at least two piezoelectric elements.

5. The transducer of claim 1, wherein in the stack, an electrode of a first polarity of a first piezoelectric element of the at least two piezoelectric elements is positioned adjacent to an electrode of a first polarity of a second piezoelectric element of the at least two piezoelectric elements.

6. The transducer of claim 1, wherein a first piezoelectric element of the at least two piezoelectric elements and a second of the at least two piezoelectric elements are separated by a distance in the stack, wherein the distance reduces the acoustic impendence of the transducer, and wherein the distance reduces the transfer of ultrasound from one of the at least two piezoelectric elements to an adjacent other of the at least two piezoelectric elements.

7. The transducer of claim 1, further comprising:
a lens comprising an upper surface, wherein a bottom surface of each of the at least two piezoelectric elements is coupled to the upper surface of the lens, such that the at least two piezoelectric elements are positioned parallel to each other along the upper surface of the lens,
wherein the lens is contoured to focus, diverge, or direct, ultrasound.

8. The transducer of claim 1, further comprising:
a matching layer, wherein a bottom surface of each of the at least two piezoelectric elements is coupled to the upper surface of the matching layer lens, such that the at least two piezoelectric elements are positioned parallel to each other along the upper surface of the matching layer,
wherein the matching layer is utilized by the transducer for improved acoustic transmission or improved acoustic receiving.

9. The transducer of claim 1, wherein the at least two piezoelectric elements can be driven one or more piezoelectric element at a time or each piezoelectric element separately, when the transducer is coupled to a power source.

10. The transducer of claim 1, wherein the at least two piezoelectric elements are comprised of a plurality of materials and operate at a plurality of different frequencies.

11. An ultrasound transducer, comprising:
at least two piezoelectric elements, oriented adjacent and positioned parallel to each other in a stack, wherein each of the at least two piezoelectric elements comprises:
a first side surface comprising an electrode of a first polarity;
a second side surface comprising an electrode of a second polarity, wherein the first side surface and the second side surface define a height of the piezoelectric element;
a thickness between the first side surface and the second side surface, wherein the height is at least three times greater than the thickness; and
an ultrasound transmitting surface having a smaller surface area than the surface area of each of the first and second side surfaces;
a first electrical connection between a surface of a first of the at least two piezoelectric elements of the first polarity and a surface of a second of the at least two piezoelectric elements of the first polarity; and
a second electrical connection between a surface of a first of the at least two piezoelectric elements of the second polarity and a surface of a second of the at least two piezoelectric elements of the second polarity,
wherein the at least two piezoelectric elements are oriented adjacent to each other when an entire electrode surface of the first of the at least two piezoelectric elements is adjacent to an entire electrode surface of the second of the at least two piezoelectric elements.

12. The transducer of claim 11, wherein the transducer is electrically coupled to electrical components and the electrical components are utilized to measure and record the ultrasound received signal from the transducer.

* * * * *